US010806658B2

(12) United States Patent
Takada et al.

(10) Patent No.: US 10,806,658 B2
(45) Date of Patent: Oct. 20, 2020

(54) INFORMATION PROCESSING APPARATUS AND INFORMATION PROCESSING METHOD

(71) Applicant: SONY CORPORATION, Tokyo (JP)

(72) Inventors: Kohei Takada, Tokyo (JP); Kumi Yashiro, Kanagawa (JP); Hiroko Inagaki, Kanagawa (JP)

(73) Assignee: SONY CORPORATION, Tokyo (JP)

( * ) Notice: Subject to any disclaimer, the term of this patent is extended or adjusted under 35 U.S.C. 154(b) by 4 days.

(21) Appl. No.: 15/752,928

(22) PCT Filed: Feb. 19, 2016

(86) PCT No.: PCT/JP2016/054954
§ 371 (c)(1),
(2) Date: Feb. 15, 2018

(87) PCT Pub. No.: WO2017/043101
PCT Pub. Date: Mar. 16, 2017

(65) Prior Publication Data
US 2018/0243157 A1    Aug. 30, 2018

Related U.S. Application Data

(60) Provisional application No. 62/215,311, filed on Sep. 8, 2015.

(51) Int. Cl.
*A61H 3/06*  (2006.01)
*G01S 13/88* (2006.01)
(Continued)

(52) U.S. Cl.
CPC ............. *A61H 3/061* (2013.01); *A61F 9/08* (2013.01); *A61H 3/06* (2013.01); *G01C 17/28* (2013.01);
(Continued)

(58) Field of Classification Search
None
See application file for complete search history.

(56) References Cited

U.S. PATENT DOCUMENTS 3,321,737 A * 5/1967 Russell ............... G01S 1/72
367/116
3,546,467 A * 12/1970 Benham ............. A45B 3/00
250/215

(Continued)

FOREIGN PATENT DOCUMENTS

| EP | 2487906 A1 | 8/2012 |
| JP | 55-094169 A | 7/1980 |

(Continued)

OTHER PUBLICATIONS

International Search Report and Written Opinion of PCT Application No. PCT/JP2016/054954, dated May 17, 2016, 09 pages.

*Primary Examiner* — Steven Lim
*Assistant Examiner* — Muhammad Adnan
(74) *Attorney, Agent, or Firm* — Chip Law Group

(57) ABSTRACT

An information processing apparatus including a processing unit that sets, on a basis of acquired input information, a feedback target range in which an object existing on inside serves as a target to be fed back to a user, in which the processing unit outputs information regarding the set feedback target range to an output unit.

14 Claims, 9 Drawing Sheets

(51) Int. Cl.
  *G01C 21/20* (2006.01)
  *G01S 15/88* (2006.01)
  *G01S 7/56* (2006.01)
  *A61F 9/08* (2006.01)
  *G01C 17/28* (2006.01)
  *G01P 15/18* (2013.01)

(52) U.S. Cl.
  CPC ............. *G01C 21/20* (2013.01); *G01P 15/18* (2013.01); *G01S 7/56* (2013.01); *G01S 13/88* (2013.01); *G01S 15/88* (2013.01); *A61H 2003/063* (2013.01); *A61H 2201/5058* (2013.01); *A61H 2201/5084* (2013.01)

(56) References Cited

U.S. PATENT DOCUMENTS

| | | | | |
|---|---|---|---|---|
| 4,280,204 | A * | 7/1981 | Elchinger | A61H 3/061 135/76 |
| 4,712,003 | A * | 12/1987 | Ban | A61F 9/08 250/215 |
| 4,858,125 | A * | 8/1989 | Washizuka | A45B 3/00 600/301 |
| 5,060,062 | A * | 10/1991 | Dotson | A61F 9/08 348/62 |
| 5,724,313 | A * | 3/1998 | Burgess | A61H 3/061 367/102 |
| 5,748,141 | A * | 5/1998 | Hoess | G01S 7/023 342/109 |
| 5,760,950 | A * | 6/1998 | Maly | G02B 21/0028 359/368 |
| 5,807,111 | A * | 9/1998 | Schrader | A61F 9/08 367/116 |
| 5,977,906 | A * | 11/1999 | Ameen | G01S 13/931 342/174 |
| 6,055,048 | A * | 4/2000 | Langevin | A61H 3/061 356/237.1 |
| 6,198,395 | B1 * | 3/2001 | Sussman | A61F 9/08 340/407.1 |
| 6,298,010 | B1 * | 10/2001 | Ritz | A61H 3/061 367/116 |
| 6,469,956 | B1 * | 10/2002 | Zeng | G01S 7/521 367/116 |
| 6,489,605 | B1 * | 12/2002 | Ritz | A61F 9/08 250/221 |
| 7,308,314 | B2 * | 12/2007 | Havey | A61F 9/08 607/54 |
| 7,598,976 | B2 * | 10/2009 | Sofer | G09B 21/006 348/62 |
| 7,778,112 | B2 * | 8/2010 | Behm | A61H 3/061 135/911 |
| 8,120,521 | B2 * | 2/2012 | Bandhauer | A61H 3/061 342/24 |
| 9,201,143 | B2 * | 12/2015 | Slamka | G01S 19/14 |
| 9,542,824 | B2 * | 1/2017 | Beggs | B60Q 1/2673 |
| 9,922,236 | B2 * | 3/2018 | Moore | G06K 9/00201 |
| 9,953,547 | B2 * | 4/2018 | Harish | G09B 21/007 |
| 10,113,877 | B1 * | 10/2018 | Schaefer | G06F 3/016 |
| 10,571,715 | B2 * | 2/2020 | Rizzo, III | A61H 3/061 |
| 10,645,519 | B2 * | 5/2020 | Koga | H04S 7/304 |
| 2005/0240253 | A1 * | 10/2005 | Tyler | A61B 5/0492 607/134 |
| 2006/0147197 | A1 * | 7/2006 | Spruck | G09B 21/008 396/429 |
| 2006/0220943 | A1 * | 10/2006 | Schlick | G01S 13/50 342/70 |
| 2006/0289624 | A1 * | 12/2006 | Olmos | A61F 9/08 235/375 |
| 2010/0152600 | A1 * | 6/2010 | Droitcour | A61B 5/05 600/534 |
| 2011/0228980 | A1 * | 9/2011 | Ichikawa | H04N 7/181 382/103 |
| 2012/0127291 | A1 * | 5/2012 | Mahoney | A61H 3/061 348/62 |
| 2012/0242801 | A1 * | 9/2012 | Barnes | A61N 1/36046 348/46 |
| 2013/0039152 | A1 * | 2/2013 | Liu | A61F 9/08 367/99 |
| 2013/0044005 | A1 * | 2/2013 | Foshee | G09B 21/007 340/691.1 |
| 2013/0250078 | A1 * | 9/2013 | Levy | A61F 9/08 348/62 |
| 2014/0132388 | A1 * | 5/2014 | Alalawi | G09B 21/003 340/4.12 |
| 2015/0063610 | A1 * | 3/2015 | Mossner | H04S 5/005 381/307 |
| 2015/0070479 | A1 * | 3/2015 | Yu | G09B 21/003 348/62 |
| 2015/0223731 | A1 * | 8/2015 | Sahin | A61B 5/16 600/301 |
| 2016/0026253 | A1 * | 1/2016 | Bradski | G02B 27/0172 345/8 |
| 2016/0077202 | A1 * | 3/2016 | Hirvonen | G01S 13/90 342/25 R |
| 2016/0084952 | A1 * | 3/2016 | Karlapalem | G01S 13/08 342/118 |
| 2016/0171303 | A1 * | 6/2016 | Moore | G06K 9/00671 382/153 |
| 2016/0265917 | A1 * | 9/2016 | Yamamoto | G01C 21/3655 |
| 2017/0087023 | A1 * | 3/2017 | Peli | A61H 3/061 |
| 2017/0261334 | A1 * | 9/2017 | Lee | G01C 21/206 |
| 2018/0021207 | A1 * | 1/2018 | Xu | A61H 3/06 340/4.12 |
| 2018/0078444 | A1 * | 3/2018 | Gamerman | A61H 3/061 |
| 2018/0110672 | A1 * | 4/2018 | Kasravi | A61H 3/061 |
| 2019/0049977 | A1 * | 2/2019 | Dean | G05D 1/0219 |
| 2019/0155404 | A1 * | 5/2019 | Cutrell | G06F 3/016 |

FOREIGN PATENT DOCUMENTS

| | | |
|---|---|---|
| JP | 55-94169 A | 7/1980 |
| JP | 56-119248 A | 9/1981 |
| JP | 57-191144 A | 11/1982 |
| JP | 59-105587 A | 6/1984 |
| JP | 02-216081 A | 8/1990 |
| JP | 03-263199 A | 11/1991 |
| JP | 2000-298800 A | 4/1999 |
| JP | 2007-240384 A | 9/2007 |
| JP | 2010-158472 A | 7/2010 |
| JP | 2012-093834 A | 5/2012 |
| JP | 2013-226345 A | 11/2013 |
| WO | 2011/043006 A1 | 4/2011 |

\* cited by examiner

FIG. 9
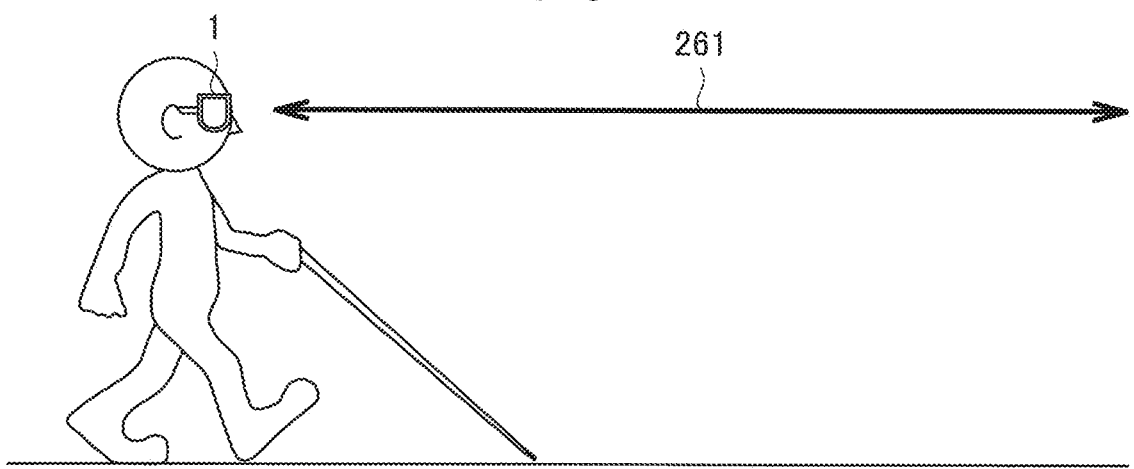
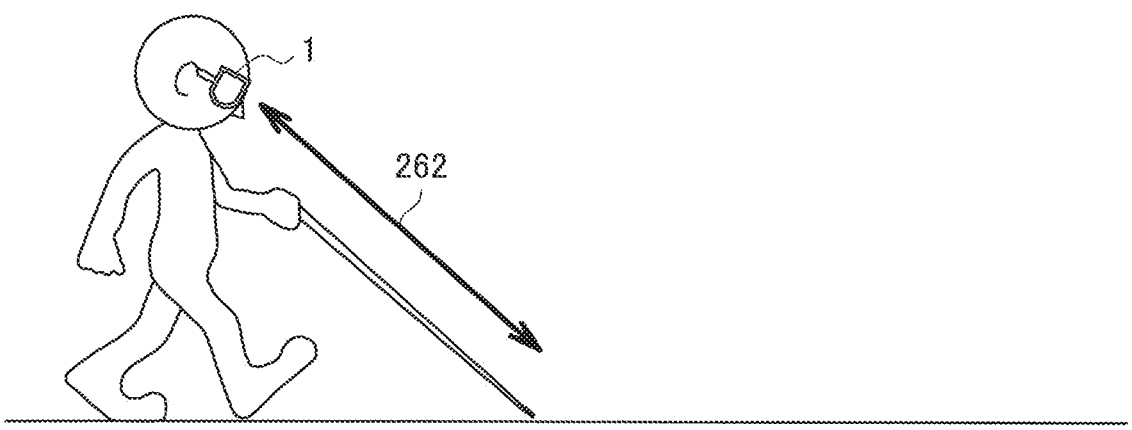

FIG. 10
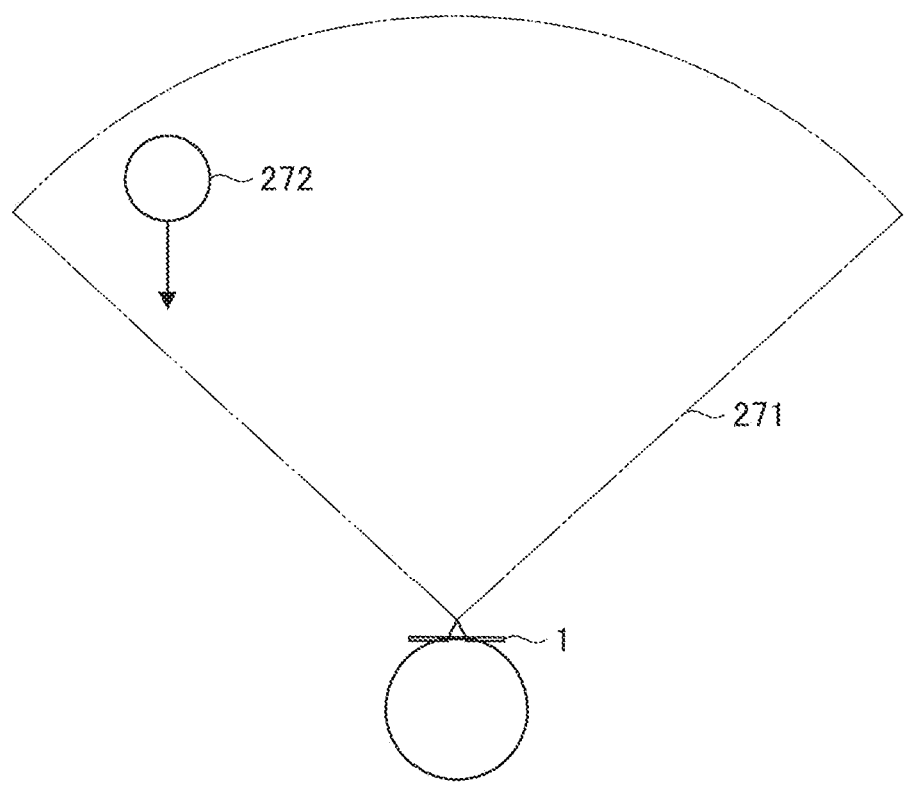
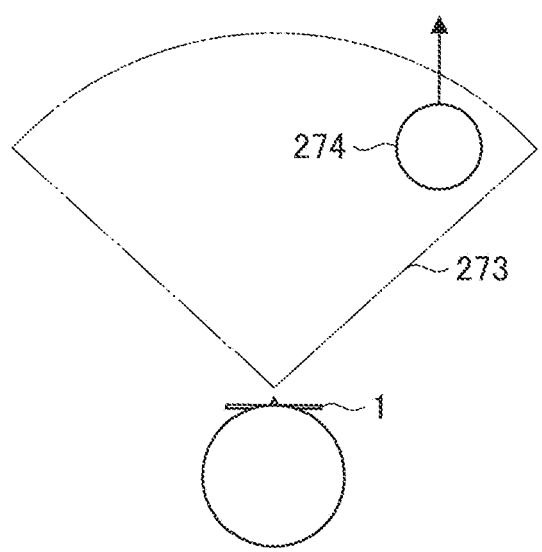

INFORMATION PROCESSING APPARATUS AND INFORMATION PROCESSING METHOD

CROSS REFERENCE TO RELATED APPLICATIONS

This application is a U.S. National Phase of International Patent Application No. PCT/JP2016/054954 filed on Feb. 19, 2016, which claims priority benefit of U.S. Patent Application No. 62/215,311 filed on Sep. 8, 2015. Each of the above-referenced applications is hereby incorporated herein by reference in its entirety.

TECHNICAL FIELD

The present disclosure relates to an information processing apparatus, an information processing method, and a program.

BACKGROUND ART

In recent years, a technology for further improving a living environment of a user has been energetically developed. An example thereof is a technology for supporting a daily life, such as walking, of a visually impaired person. There are many obstructions that cannot be easily detected by using a white cane that has been conventionally and widely used, and therefore it is desired to develop a technology for detecting such obstructions to compensate for a weakness of the white cane.

In another field, for example, a technology for improving a driving environment of a vehicle has also been developed. For example, Patent Literature 1 cited below discloses a technology of restricting a measurement range of a measurement instrument for measuring a distance between two vehicles only at the time of driving in a curve, thereby preventing an obstruction such as a guardrail from being mistakenly detected in the curve without detecting a vehicle running ahead.

CITATION LIST

Patent Literature

Patent Literature 1: JP 2000-298800A

DISCLOSURE OF INVENTION

Technical Problem

A technology for compensating for a weakness of a white cane is, for example, a technology of giving a notice to a user in a case where a distance from an obstruction existing in the vicinity of the user is measured and the obstruction exists in a predetermined distance. However, which obstruction the user should be notified of may be different depending on a situation of the user. In view of this, it is desirable to provide a system capable of appropriately performing setting regarding an obstruction which the user should be notified of.

Solution to Problem

According to the present disclosure, there is provided an information processing apparatus including a processing unit configured to set, on a basis of acquired input information, a feedback target range in which an object existing on inside serves as a target to be fed back to a user, in which the processing unit outputs information regarding the set feedback target range to an output unit.

Further, according to the present disclosure, there is provided an information processing method including: setting, by a processor to set, on a basis of acquired input information, a feedback target range in which an object existing on inside serves as a target to be fed back to a user; and outputting information regarding the set feedback target range to an output unit.

Further, according to the present disclosure, there is provided a program causing a computer to function as an information processing apparatus including a processing unit configured to set, on a basis of acquired input information, a feedback target range in which an object existing on inside serves as a target to be fed back to a user, in which the processing unit outputs information regarding the set feedback target range to an output unit.

Advantageous Effects of Invention

As described above, the present disclosure provides a system capable of appropriately performing setting regarding an obstruction which a user should be notified of. Note that the effects described above are not necessarily limitative. With or in the place of the above effects, there may be achieved any one of the effects described in this specification or other effects that may be grasped from this specification.

BRIEF DESCRIPTION OF DRAWINGS

FIG. 9 is an explanatory view for describing an example of setting of a feedback target range based on a posture of a user.

FIG. 10 is an explanatory view for describing an example of setting of a feedback target range based on a relative speed of an object.

MODE(S) FOR CARRYING OUT THE INVENTION

Figure 1:
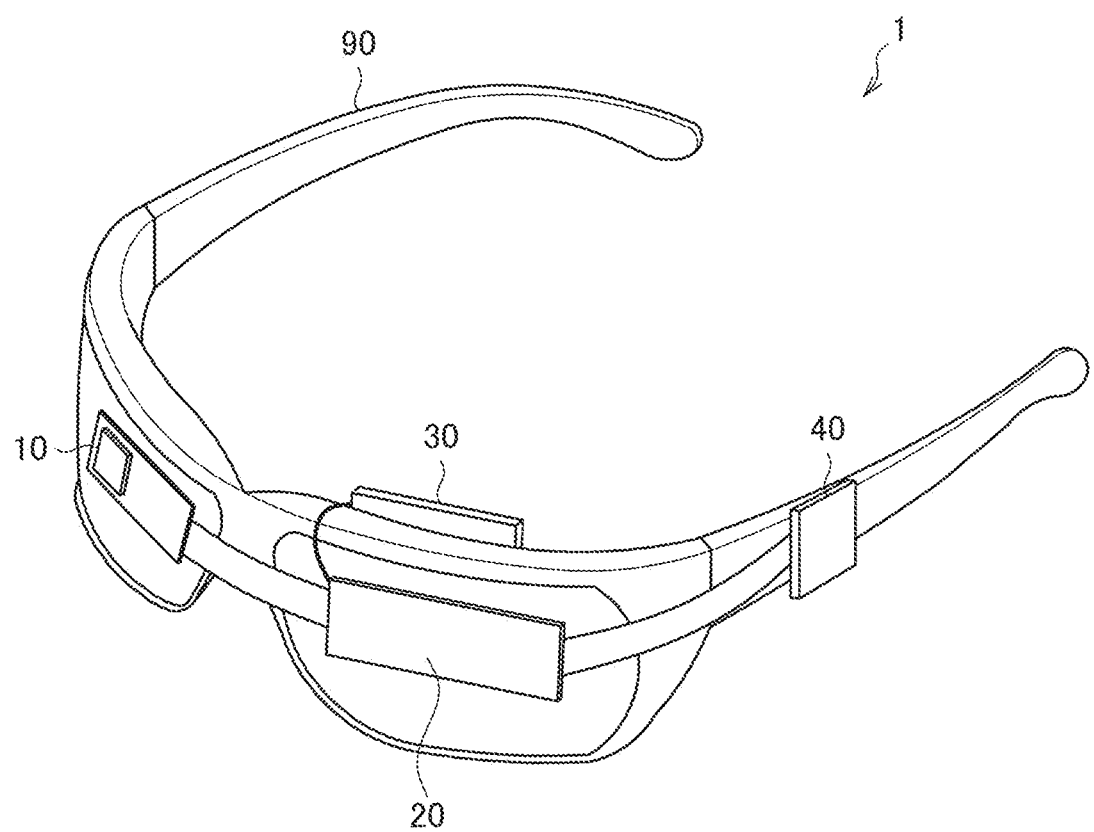
FIG. 1 is an explanatory view for describing an example of an exterior configuration of an information processing apparatus according to the present embodiment.

Hereinafter, (a) preferred embodiment(s) of the present disclosure will be described in detail with reference to the appended drawings. Note that, in this specification and the appended drawings, structural elements that have substantially the same function and structure are denoted with the same reference numerals, and repeated explanation of these structural elements is omitted.

Note that description will be provided in the following order.

1. Configuration example
   1.1. Hardware configuration example
   1.2. Functional configuration example
2. Flow of Processing
3. Setting example of feedback target range
4. Conclusion <<1. Configuration Example>>

First, a configuration example of an information processing apparatus according to an embodiment of the present disclosure will be described with reference to FIGS. 1 to 3.

<1.1. Hardware Configuration Example>

FIG. 1 is an explanatory view for describing an example of an exterior configuration of an information processing apparatus 1 according to the present embodiment. In the example illustrated in FIG. 1, the information processing apparatus 1 is integrally provided with eyeglasses 90 and is mounted on a head of a user. The information processing apparatus 1 includes a distance measurement sensor 10, an electronic circuit 20, a vibrator 30, and a battery 40.

Figure 2:
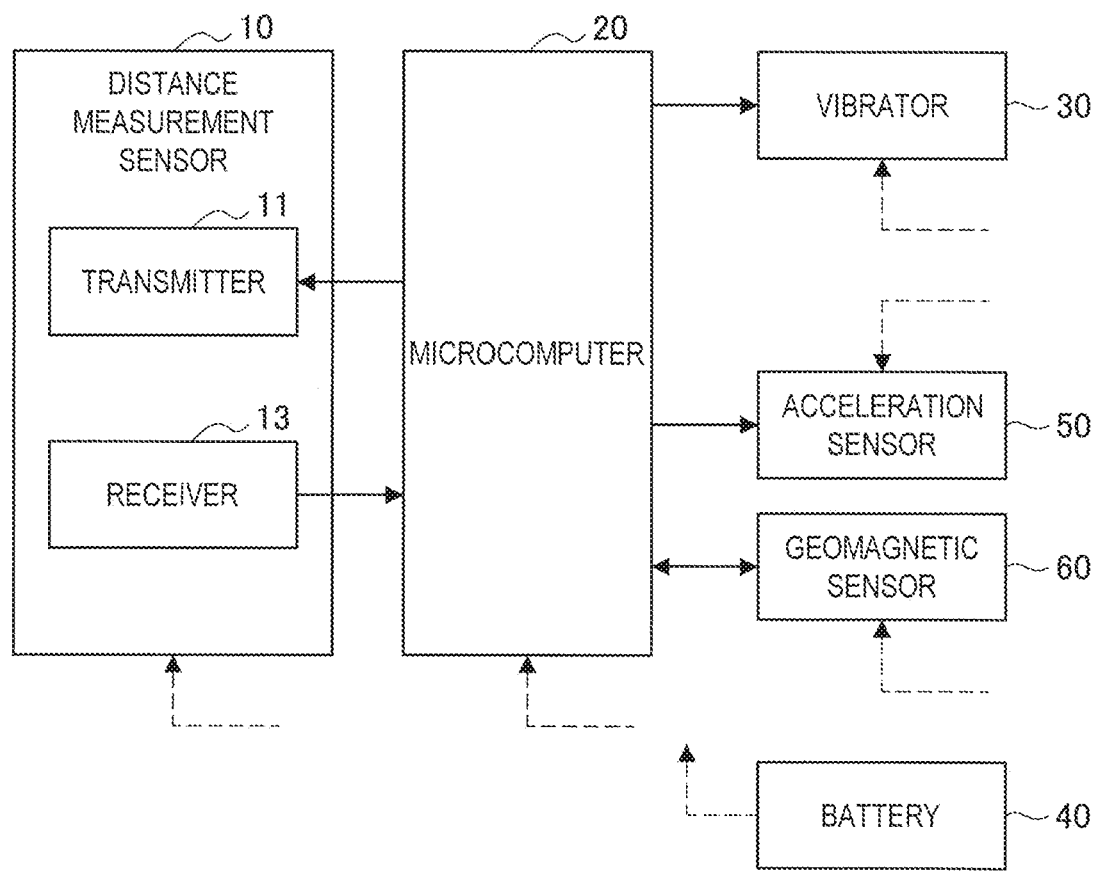
FIG. 2 is a block diagram showing an example of an internal configuration of the information processing apparatus according to the present embodiment.

FIG. 2 is a block diagram showing an example of an internal configuration of the information processing apparatus 1 according to the present embodiment. As illustrated in FIG. 2, the information processing apparatus 1 includes an acceleration sensor 50 and a geomagnetic sensor 60 which are not illustrated in FIG. 1.

The distance measurement sensor 10 is a device for measuring a distance from an object existing in a surrounding environment. The distance measurement sensor 10 may be realized by, for example, a sonic sensor, an ultrasonic sensor, a radio wave sensor, a stereo camera, an image sensor of a time-of-flight (TOF) method, or the like. As illustrated in FIG. 2, the distance measurement sensor 10 may include a transmitter 11 for transmitting a sonic wave, an ultrasonic wave, light, or the like and a receiver 13 for receiving a reflected wave obtained by causing a transmission wave from the transmitter 11 to be reflected by an object (i.e., obstruction). The distance measurement sensor 10 measures a distance from an object on the basis of a relationship (e.g., phase difference) between a transmission wave and a reflected wave.

The vibrator 30 is a device that vibrates on the basis of control by the electronic circuit 20.

The battery 40 is a device for supplying power to each device included in the information processing apparatus 1, such as the distance measurement sensor 10, the electronic circuit 20, the vibrator 30, the acceleration sensor 50, and the geomagnetic sensor 60.

The acceleration sensor 50 is a device for measuring acceleration. The acceleration sensor 50 measures acceleration regarding the information processing apparatus 1. For example, the acceleration sensor 50 may be a three-axis acceleration sensor.

The geomagnetic sensor 60 is a device for measuring geomagnetism. The geomagnetic sensor 60 may be a so-called electromagnetic compass and can measure an orientation in which the information processing apparatus 1 faces.

The electronic circuit 20 is a device for controlling each device included in the information processing apparatus 1. As illustrated in FIG. 2, the electronic circuit 20 may be realized by a microcomputer 20. Further, the electronic circuit 20 may be realized by a central processing unit (CPU) or a micro-processing unit (MPU). For example, the electronic circuit 20 acquires sensor information obtained by various sensors such as the distance measurement sensor 10, the acceleration sensor 50, and the geomagnetic sensor 60 and performs various kinds of processing, thereby causing the vibrator 30 to vibrate in accordance with processing results.

Hereinabove, the hardware configuration example of the information processing apparatus 1 has been described. Note that the exterior configuration illustrated in FIG. 1 is an example and the present technology is not limited to such an example. For example, the information processing apparatus 1 may be mounted on a white cane, may be mounted on a belt, or may be realized in various forms such as a head mounted display (HMD) type, a pendant type, or a watch type. Further, the information processing apparatus 1 may be realized as a non-wearable device such as a smartphone.

Further, the use of the information processing apparatus 1 is not limited to an obstruction detector for a visually impaired person or mildly visually impaired person. For example, the information processing apparatus 1 may also be used as, for example, an obstruction detector in the dark to assist an able-bodied person to work. Further, the information processing apparatus 1 may be used for a game or may be attached to a drone, a door, or the like to be used to prevent crimes.

<1.2. Functional Configuration Example>

Figure 3:
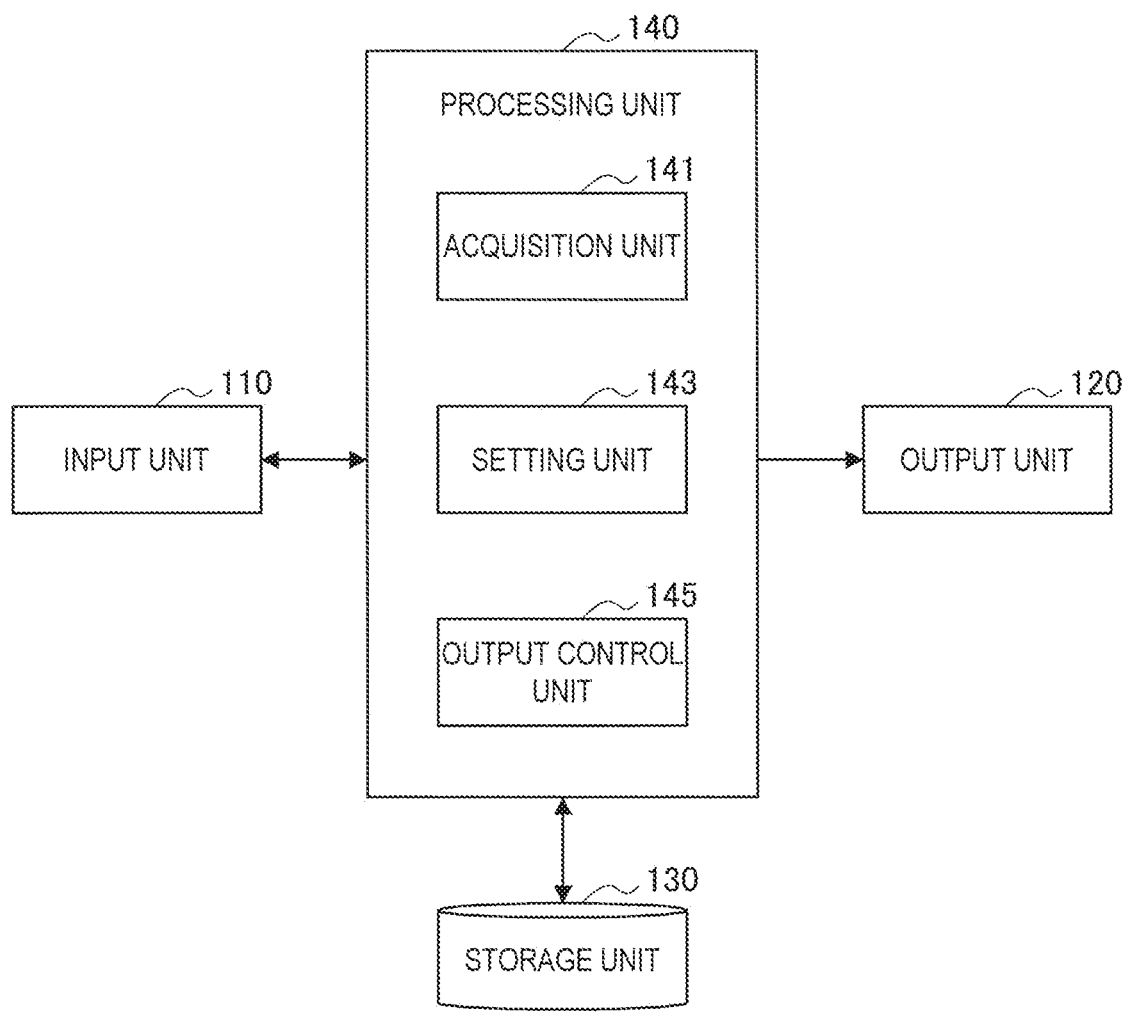
FIG. 3 is a block diagram showing an example of a logical functional configuration of the information processing apparatus according to the present embodiment.

FIG. 3 is a block diagram showing an example of a logical functional configuration of the information processing apparatus 1 according to the present embodiment. As illustrated in FIG. 3, the information processing apparatus 1 includes an input unit 110, an output unit 120, a storage unit 130, and a processing unit 140.

The input unit 110 has a function of accepting input of various kinds of information. Specifically, the input unit 110 corresponds to the distance measurement sensor 10 (i.e., distance measurement unit), the acceleration sensor 50, and the geomagnetic sensor 60. The input unit 110 may include not only those sensors but also, for example, an arbitrary sensor such as an image sensor or a gyro sensor. Hereinafter, the information input to the input unit 110 will also be referred to as "input information". The input unit 110 outputs the input information to the processing unit 140.

The output unit 120 has a function of outputting various kinds of information on the basis of control by the processing unit 140. Specifically, the output unit 120 corresponds to the vibrator 30. The output unit 120 may include not only the vibrator 30 but also, for example, an audio output device such as a speaker or earphones or may include a display device capable of outputting an image such as a display. Audio output is also useful for a visually impaired person, and image output is also useful for a mildly visually impaired person or able-bodied person. In addition, the output unit 120 may include a device that performs output by using haptics, a smell, a taste, a lamp (e.g., light emitting diode (LED)), or the like.

The storage unit 130 temporarily or permanently stores programs and various data for operating the information processing apparatus 1.

The processing unit 140 provides various functions of the information processing apparatus 1. Specifically, the processing unit 140 corresponds to the electronic circuit 20. As illustrated in FIG. 3, the processing unit 140 includes an acquisition unit 141, a setting unit 143, and an output control unit 145. Note that the processing unit 140 may further include other constituent elements in addition to those constituent elements. That is, the processing unit 140 may also perform operation of other constituent elements in addition to operation of those constituent elements.

Details of functions of the acquisition unit 141, the setting unit 143, and the output control unit 145 will be described in detail below.

(1) Acquisition of Input Information

The information processing apparatus 1 (e.g., the acquisition unit 141) acquires input information. The input information may include information regarding sensor information. The information regarding sensor information includes not only raw sensor information but also information obtained by processing or interpreting the raw sensor information. For example, the input information may be information regarding a distance (i.e., relative distance) from the user to the object. In addition, this information regarding a relative distance may be information indicating a relative distance itself obtained by the distance measurement sensor 10, may be a relative speed of the object obtained by differentiating the relative distance, or may be relative acceleration of the object obtained by differentiating the relative distance twice.

There are various kinds of input information. Hereinafter, examples of the input information will be described.

The input information may include, for example, information regarding the user. For example, the input information may include a fixation point (e.g., line-of-sight direction or focus), a position of a tip of a white cane, behavior information (e.g., stopping, walking, running, ascending and descending stairs, driving automobile, or the like), or information regarding a moving speed. Further, the input information may include information regarding biological information (e.g., heartbeat, body temperature, perspiration, blood pressure, perspiration, pulse, respiration, nictation, eye movement, staring time, size of pupil diameter, blood pressure, brain wave, body movement, body position, skin temperature, electrical skin resistance, micro vibration (MV), muscle potential, and $SPO_2$ (blood oxygen saturation)). Further, the input information may include emotional information (e.g., joy, anger, grief, and pleasure), a posture of the user (e.g., direction of head), profile information of the user (e.g., age, sex, and the like), a position of the user, or information regarding a user setting input by the user. Further, the input information may include information on a network such as a friendship on a social networking service (SNS), a behavior history, and information regarding a use state or the like of a device (i.e., the information processing apparatus 1).

The input information may include information regarding the object. For example, the input information may include information regarding a size, a position, a posture, hardness, a state (e.g., moving speed, moving direction, track, update frequency, and the like), or an attribute (type, degree of danger, and the like) of the object.

The input information may include information regarding an environment. For example, the input information may include information regarding a background (e.g., important information existing in surrounding environment, scenery of surrounding environment, and background color), illuminance, a place (e.g., inside/outside, and situation (geofence)), a behavior history (e.g., whether or not the user is in familiar place), a peripheral situation (e.g., presence/absence and density of objects such as other people or vehicles in the vicinity of the user), time, an altitude, an air temperature, a wind direction, a flow rate, or the like.

The input information may include information regarding the device (i.e., the information processing apparatus 1). For example, the input information may include information regarding an attribute of the device (e.g., eyeglass-type, HMD, smartphone, or the like), a characteristic of the output unit 120 (e.g., display resolution, display size, HMD method, or the like), presence/absence of a sensor, an ID, a residual quantity of a battery, a battery capacity, whether or not charging is currently performed, a processing load of a CPU, a temperature of the CPU, presence/absence of an external storage medium slot, a communication method, an acoustic characteristic, a characteristic of an imager, a 3D imaging ability, a 3D display ability, or the like. Further, the input information may include information regarding a posture of the device, a mounting state (e.g., mounted, not mounted, and a mounting place) in a case of a wearable device, or a position of the device (e.g., mounting position in a case of wearable device).

(2) Feedback Target Range

The information processing apparatus 1 (e.g., the setting unit 143) sets a feedback target range. The feedback target range is a range (e.g., space) in which an object existing on the inside thereof serves as a target to be fed back to the user. As described in detail below, the information processing apparatus 1 sets a feedback target range on the basis of the input information. With this, the information processing apparatus 1 can flexibly change the feedback target range in accordance with a situation of the user (e.g., state of the user, behavior of the user, surrounding environment, or the like) and can provide appropriate feedback (e.g., warning). Note that setting of a feedback target range is a concept including not only setting of a size, shape, or the like of the feedback target range but also on/off of a feedback function itself. Furthermore, setting of a feedback target range may be a concept including specification or exclusion of an object serving as a target to be fed back (e.g., warning). The information processing apparatus 1 can changeably set a feedback target range, and therefore the user can save complicated labor to manually set a feedback target range.

Herein, a complementary relationship between the information processing apparatus 1 and a white cane will be described with reference to FIG. 4.

Figure 4:
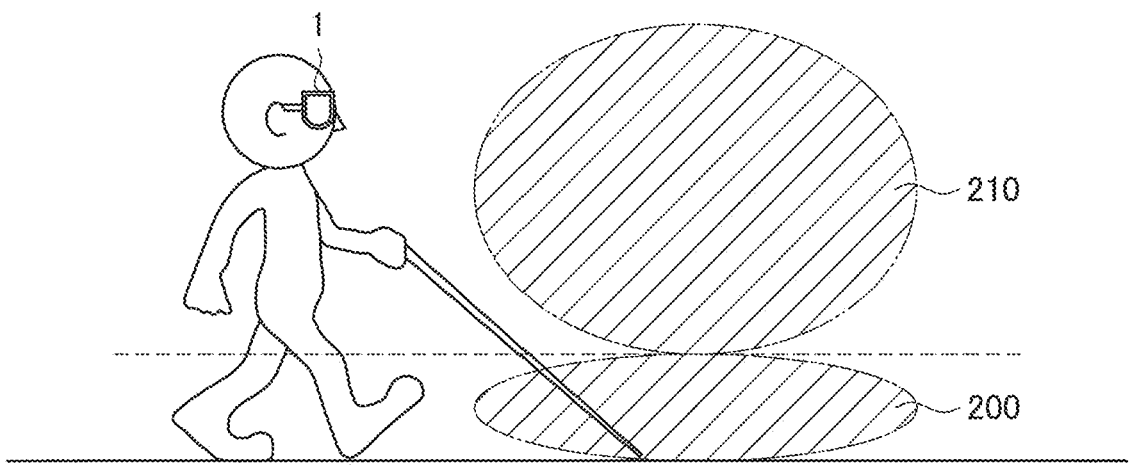
FIG. 4 is an explanatory view for describing a complementary relationship between the information processing apparatus according to the present embodiment and a white cane.

FIG. 4 is an explanatory view for describing a complementary relationship between the information processing apparatus 1 according to the present embodiment and a white cane. The white cane is effective in detecting an obstruction existing in a space 200 around feet. Meanwhile, it is difficult to detect an obstruction existing in a space 210 above knees by using the white cane. In view of this, by setting the space 210 above knees as a feedback target range, the information processing apparatus 1 can detect an obstruction that cannot be easily detected by using the white cane. As described above, the user can defend himself/herself against a surrounding obstruction by using both the white cane and the information processing apparatus 1.

Hereinafter, a feedback target range will be specifically described with reference to FIG. 5.

Figure 5:
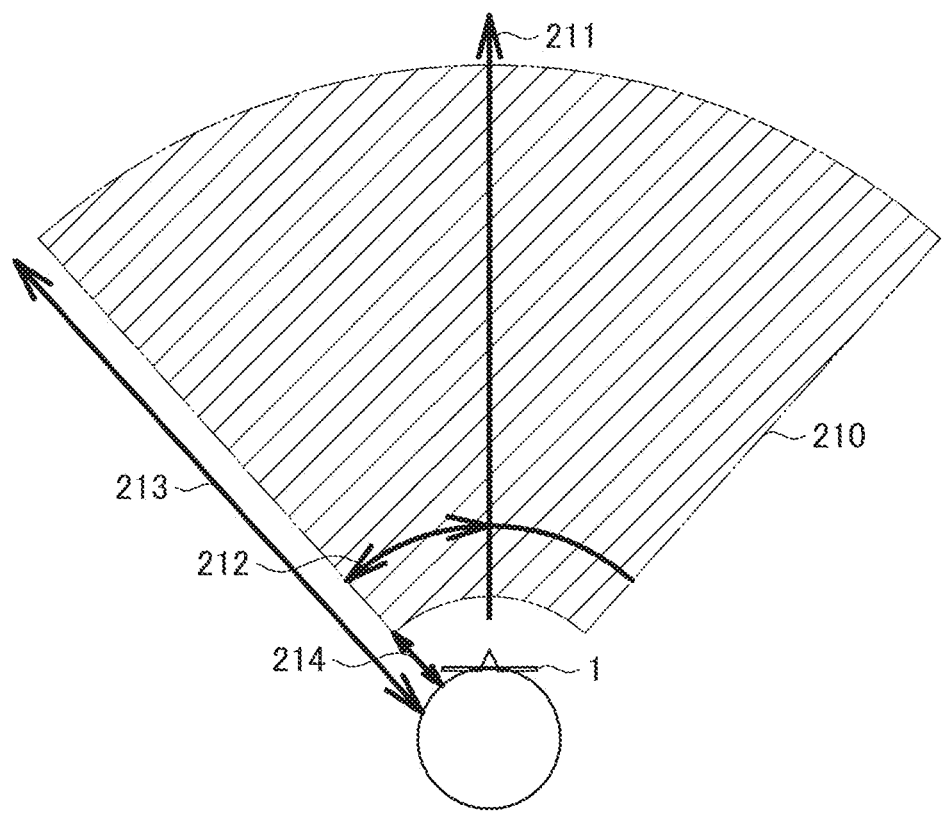
FIG. 5 is an explanatory view for describing an example of a feedback target range set by the information processing apparatus according to the present embodiment.

FIG. 5 is an explanatory view for describing an example of a feedback target range 210 set by the information processing apparatus 1 according to the present embodiment. The information processing apparatus 1 (e.g., the setting unit 143) may set a first threshold (i.e., maximum distance) 213 regarding a distance from the user and set a range in which the distance from the user is less than or equal to the maximum distance 213 or is less than the maximum distance 213 as the feedback target range 210. With this, the user can detect, for example, only an obstruction existing in a distance at which the user may collide with the obstruction. Further, the information processing apparatus 1 may set a third threshold (i.e., maximum angle) 212 regarding an angle from a front direction 211 of the user and set a range in which the angle from the front direction 211 of the user is less than or equal to the maximum angle 212 as the feedback target range 210. With this, the user can detect, for example, only an obstruction existing in a direction in which the user may collide with the obstruction. Note that the front direction 211 may mean a direction in which a face or a body is directed or may mean a moving direction in a case where the user is moving. Further, the angle from the front direction 211 of the user may mean an angle in a horizontal direction (i.e., horizontal width seen from the user) or may mean an angle in a vertical direction (i.e., vertical width seen from the user). That is, the feedback target range may be set as a three-dimensional space. Further, the information processing apparatus 1 may set a second threshold (i.e., minimum distance) 214 regarding a distance from the user and set a region in which the distance from the user is more than or equal to the minimum distance 214 or is more than the minimum distance 214 as the feedback target range 210. With this, for example, it is possible to omit a warning regarding an obstruction, a white cane, or a guide dog, which is positioned too close to the user and which the user can directly recognize with his/her hand or the like.

The feedback target range may have various shapes other than the shape illustrated in FIG. 5. For example, the feedback target range illustrated in FIG. 5 has a uniform shape whose maximum distance is not changed depending on a direction. However, the feedback target range may have a non-uniform (or can also be grasped as "nonlinear") shape. Specifically, the maximum distance may be set to be large in a case of a direction of travel of the user, a direction in which a face is directed, or a direction of a road, and the maximum distance may be set to be small in a case of a place behind or beside the user or a direction in which no road exists. The same applies to the minimum distance and the maximum angle. Further, the feedback target range illustrated in FIG. 5 is defined in a polar coordinate system having the user as the center but may be defined in, for example, an orthogonal coordinate system. Specifically, the feedback target range may be an arbitrary three-dimensional space specified by setting of coordinates, lengths, or the like on coordinate axes in a vertical direction, a horizontal direction, and a height direction. Further, the feedback target range may be defined in an arbitrary coordinate system.

The information processing apparatus 1 can changeably set a feedback target range on the basis of the input information. At that time, the information processing apparatus 1 may gradually change the feedback target range. With this, for example, it is possible to gradually expand and contract the feedback target range, and therefore it is possible to prevent the user from being confused due to abrupt expansion and contraction thereof. Further, the information processing apparatus 1 may changeably set a time interval between a change in the input information and a change in the feedback target range. For example, the information processing apparatus 1 does not need to change setting of the feedback target range for a while even in a case where the input information is changed or may change the setting thereof at the same time when the input information is changed. With this, it is possible to, for example, prevent the setting from being excessively changed or immediately change the setting. Those setting examples will be described in detail below with reference to FIG. 7.

(3) Feedback

The information processing apparatus 1 (e.g., the output control unit 145) outputs information regarding a set feedback target range to the output unit 120 and cause the output unit 120 to feed back the information to the user.

First, the information processing apparatus 1 may output information regarding an object existing in the feedback target range. This feedback can also be grasped as a warning of an obstruction. With this feedback, the user can detect the object existing in the feedback target range. This feedback is expected to be a plurality of types including a slight warning and a serious warning. For example, this feedback may be not only a serious warning to urge avoidance or a slight warning to simply giving the notice of existence but also, for example, the notice of information of an object. As a matter of course, those plurality of types of feedbacks may be combined. Further, a feedback target range may be set for each type of feedback. For example, a small feedback target range may be set for a serious warning, and a large feedback target range may be set for a slight warning.

Further, the information processing apparatus 1 may changeably control feedback in accordance with a relative relationship between the user and an obstruction. For example, the information processing apparatus 1 may control a content of the feedback in accordance with a position of the obstruction seen from the user, a relative speed thereof, a relative speed thereof, or the like. Herein, detection of the object existing in the feedback target range may be performed on the basis of distribution of distances obtained by the distance measurement sensor, an image recognition result of an image obtained by an image sensor, or the like.

Second, the information processing apparatus 1 may output information indicating the set feedback target range. This feedback can also be grasped as output of information indicating a content of setting. The feedback target range may be automatically changed. However, with this feedback, the user can grasp at any time that the user is warned of which object existing in which range (distance, width, direction, and the like). A specific output example will be described in detail below with reference to FIG. 8.

Further, the information processing apparatus 1 may output information for a route guide. For example, the information processing apparatus 1 may output an audio guide, map display, or the like for causing the user to walk with a route having a small number of obstructions.

The information processing apparatus 1 may control a timing of feedback. For example, the information processing apparatus 1 may provide feedback at a timing at which the walking is started, a timing at which caution for an obstruction is started (e.g., reducing a walking speed, frequently moving a white cane, or the like), or a timing at which the walking is stopped.

(4) Setting of Distance Measurement Range

The information processing apparatus 1 (e.g., the setting unit 143) may output information regarding a distance measurement range indicating a range in which distance measurement is performed to the distance measurement sensor 10 (i.e., measurement unit) for measuring a distance between the user and an object. This distance measurement range can also be grasped as a range in which an object is detectable. For example, the information processing apparatus 1 may output setting information of the distance measurement range (e.g., a range in which a transmission wave transmitted by the transmitter 11 can reach) so that distance measurement is performed in a narrower range in a condition in which at least the feedback target range is included. With this, the distance measurement sensor 10 can save power because it is unnecessary to perform distance measurement beyond the feedback target range.

<<2. Flow of Processing>>

Hereinafter, a flow of processing performed by the information processing apparatus 1 according to the present embodiment will be described with reference to FIG. 6.

Figure 6:
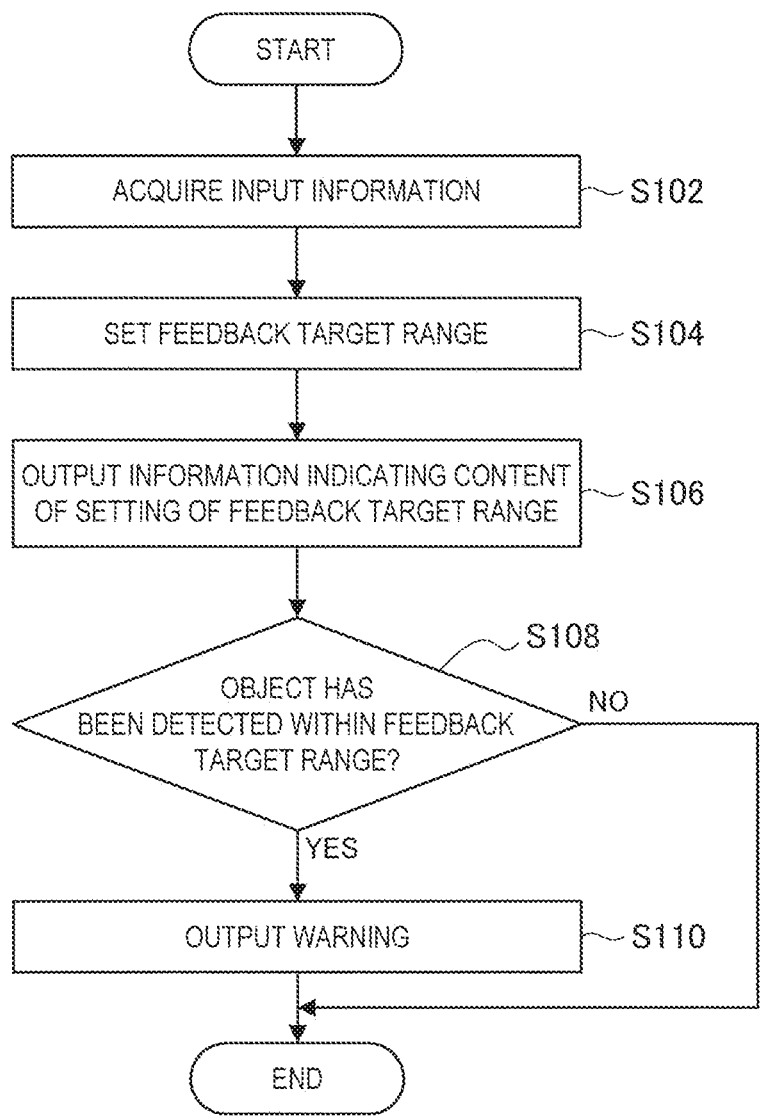
FIG. 6 is a flowchart showing an example of a flow of feedback processing executed in the information processing apparatus according to the present embodiment.

FIG. 6 is a flowchart showing an example of a flow of feedback processing executed in the information processing apparatus 1 according to the present embodiment. As illustrated in FIG. 6, first, the information processing apparatus 1 acquires input information (Step S102). Then, the information processing apparatus 1 sets a feedback target range on the basis of the input information (Step S104). Next, the information processing apparatus 1 outputs information indicating a content of setting of the feedback target range (e.g., maximum distance, minimum distance, maximum angle, or object excluded from feedback target) (Step S106). Note that the information processing apparatus 1 may omit this step in a case where the content of the setting of the feedback target range is not changed or may periodically execute this step. Then, the information processing apparatus 1 determines whether or not an object has been detected within the feedback target range (Step S108). Then, in a case where an object has been detected within the feedback target range, the information processing apparatus 1 outputs a warning (Step S110), and, in a case where no object has been detected, the information processing apparatus 1 terminates the processing without outputting any warning in particular.

<<3. Setting Example of Feedback Target Range>>

Hereinafter, a specific setting example of a feedback target range changeably set by the information processing apparatus 1 will be described.

(1) Setting Based on Moving Speed

For example, the information processing apparatus 1 may set a feedback target range on the basis of a moving speed of the user. Herein, the input information may include information regarding the moving speed of the user. The moving speed of the user may be estimated on the basis of, for example, a length of a time interval at which a single step is detected, a magnitude of an amplitude, or the like by using an output result from the acceleration sensor.

Specifically, the information processing apparatus 1 may set a larger maximum distance as the moving speed of the user is faster and may set a smaller maximum distance (including 0; that is, turning off the feedback function) as the moving speed of the user is slower. This is because there is a fear that, in a case where the maximum distance is small even though the moving speed is fast, detection of an obstruction is delayed and a collision with the obstruction may occur. For example, in a case where the maximum distance is 40 cm and the user walks at about 1 m per second, the user collides with the obstruction unless the user stops within at least 0.4 second after a warning. Regarding this point, the information processing apparatus 1 sets a large maximum distance in a case where the moving speed is fast and can therefore prevent detection of the obstruction from being delayed. Meanwhile, in a case where the maximum distance is large even though the moving speed is slow, the user is warned against a far obstruction with which the user does not probably collide, thereby disturbing the user walking. Regarding this point, the information processing apparatus 1 can prevent excessive warnings by reducing the maximum distance or turning off the feedback function in a case where the moving speed is slow such as a case where the user stops walking or a case where the user sits. Furthermore, power consumption for warning such as vibration by the vibrator 30 is reduced, and therefore it is possible to realize reduction in power.

Hereinafter, setting of a feedback target range based on the moving speed will be specifically described with reference to FIG. 7.

Figure 7:
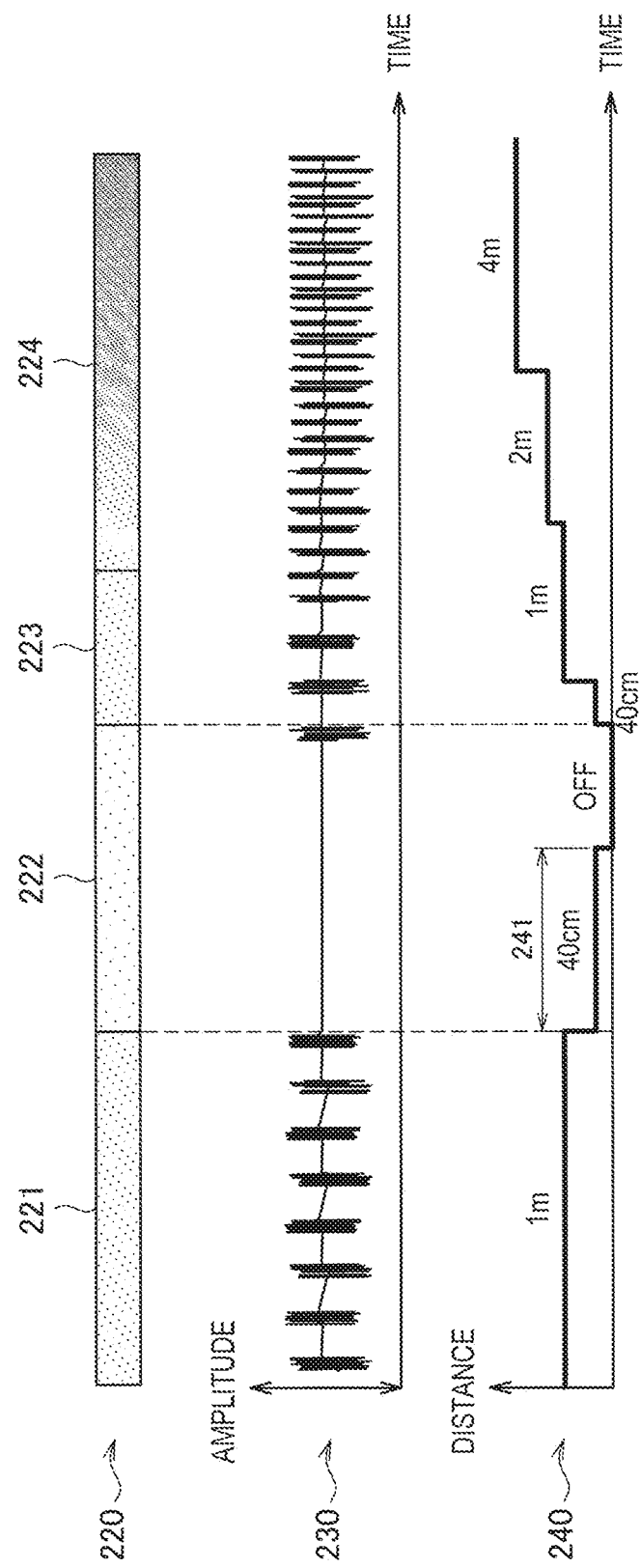
FIG. 7 is an explanatory view for describing an example of setting of a feedback target range based on a moving speed of a user.

FIG. 7 is an explanatory view for describing an example of setting of a feedback target range based on the moving speed of the user. A part denoted by a reference sign 220 indicates a walking state, and the moving speed is faster as hatching is darker. A part denoted by a reference sign 230 indicates output from the acceleration sensor 50, and a horizontal axis shows time and a vertical axis shows an amplitude. A timing at which this amplitude is observed indicates a timing of a single step in walking and means that the user walks more slowly as an interval is longer and means that the user walks faster as the interval is shorter. For example, the user walks slowly in a section 221 in which intervals between which amplitudes are observed are long. The user stops in a section 222 in which no amplitude is observed. The user walks slowly in a section 223 in which intervals between which amplitudes are observed are long. The user walks gradually faster in a section 224 in which intervals between which amplitudes are observed are gradually reduced.

A part denoted by a reference sign 240 indicates a maximum distance of a feedback target range, and a horizontal axis shows time and a vertical axis shows a distance. The maximum distance is 1 m in the section 221, and, when the user stops and enters the section 222, the maximum distance is reduced to 40 cm, and the maximum distance becomes 0 m (i.e., the feedback function is turned off) after predetermined time 241 elapses. As described above, the maximum distance may be gradually changed. Alternatively, the maximum distance does not immediately become 0 m even in a case where the user stops, and a time interval may be set to between a time point at which stop is detected and a time point at which the maximum distance becomes 0 m. Further, when the user restarts walking and enters the section 223, the maximum distance is gradually increased and becomes 1 m, and thereafter the maximum distance is gradually extended to 2 m and then 4 m as the user increases a walking pace.

Herein, a feedback example will be described continuously with reference to FIG. 7.

In a case where an object exists within the set maximum distance, the information processing apparatus 1 outputs a warning. For example, in the section 221, a warning is output in a case where an object exists within 1 m from the user. This warning may be output in various forms such as vibration, audio output, or image output.

Further, the information processing apparatus 1 may output information indicating the set feedback target range. For example, when the information processing apparatus 1 enters the section 222 and the maximum distance is set to 40 cm, the information processing apparatus 1 may output audio "A detection distance becomes 40 cm". Further, when the predetermined time 241 elapses and the feedback function is turned off, the information processing apparatus 1 may output audio "Detection is stopped". Further, when the information processing apparatus 1 enters the section 223 and the maximum distance is set to 40 cm, the information processing apparatus 1 may output audio "Detection is restarted and a detection distance is 40 cm". Instead of audio output, information indicating a content of setting of the feedback target range may be output in the form of an image as illustrated in FIG. 8.

Figure 8:
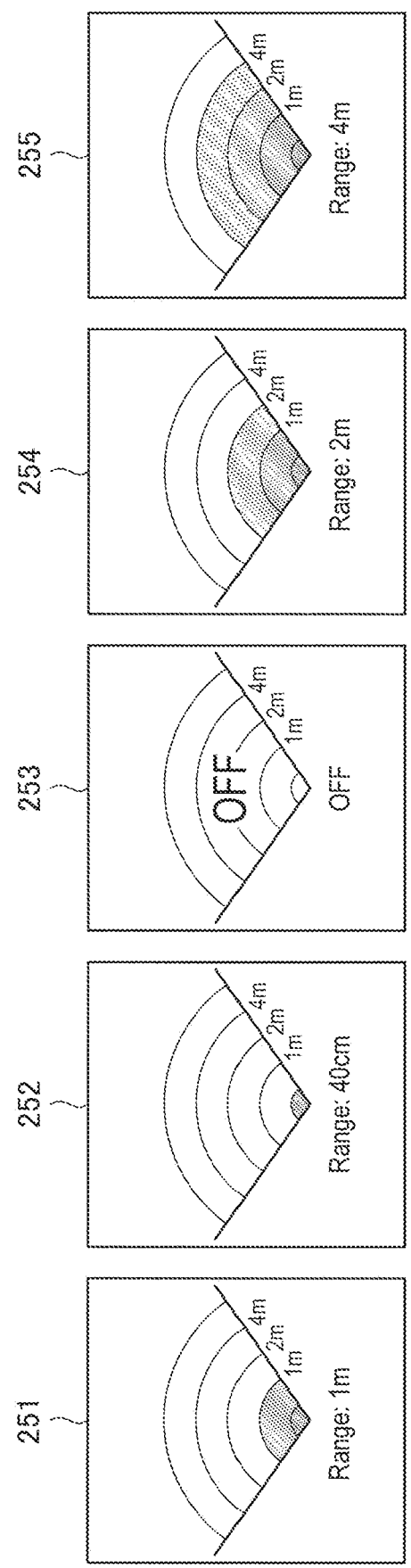
FIG. 8 is an explanatory view for describing an example of output of an image showing a content of setting of a feedback target range.

FIG. 8 is an explanatory view for describing an example of output of an image showing a content of setting of a feedback target range. For example, when the information processing apparatus 1 enters the section 221 and the maximum distance is set to 1 m, the information processing apparatus 1 outputs an image 251, and, when the information processing apparatus 1 enters the section 222 and the maximum distance is set to 40 cm, the information processing apparatus 1 outputs an image 252. When the predetermined time 241 elapses and the feedback function is turned off, the information processing apparatus 1 outputs an image 253. Thereafter, when the information processing apparatus 1 enters the section 223 and the maximum distance is set to 40 cm, the information processing apparatus 1 outputs the image 252, and, when the maximum distance is set to 1 m, the information processing apparatus 1 outputs the image 251. Then, when the information processing apparatus 1 enters the section 224 and the maximum distance is set to 2 m, the information processing apparatus 1 outputs an image 254, and, when the maximum distance is set to 4 m, the information processing apparatus 1 outputs an image 255.

(2) Setting Based on Posture

For example, the information processing apparatus 1 may set a feedback target range on the basis of a posture of the user. Herein, the input information may include information regarding the posture of the user. The posture of the user may be estimated on the basis of, for example, an output result from the gyro sensor or the geomagnetic sensor. In a case where the information processing apparatus 1 is expected to be mounted on the head of the user, the posture of the user can also be grasped as a direction of the head of the user.

Specifically, as illustrated in FIG. 9, the information processing apparatus 1 may set a smaller maximum distance as the user is directed toward a ground side from the horizontal direction. FIG. 9 is an explanatory view for describing of an example of setting of a feedback target range based on the posture of the user. A reference sign 261 denotes a maximum distance set in a case where the head of the user is directed in the horizontal direction, and a reference sign 262 denotes a maximum distance set in a case where the head of the user is directed toward the ground side from the horizontal direction. As described above, a small maximum distance is set in a case where the user is directed toward the ground side, and therefore it is possible to prevent a warning from being output because the ground is recognized as an obstruction. Further, it is also possible to prevent a warning from being output because a white cane or guide dog is recognized as an obstruction. Note that the maximum distance denoted by the reference sign 262 is desirably less than or equal to a height of the user and may be, for example, about 1.2 m.

(3) Setting Based on Relative Speed

For example, the information processing apparatus 1 may set a feedback target range on the basis of a relative speed between an object and the user. Herein, the input information may include information regarding the relative speed between the object and the user. The moving speed of the user may be estimated on the basis of, for example, a differential value of a distance between the object and the user obtained by the distance measurement sensor.

Specifically, as illustrated in FIG. 10, the information processing apparatus 1 may set a larger maximum distance as a speed at which an object approaches the user is faster and set a smaller maximum distance as the speed at which the object approaches the user is slower. FIG. 10 is an explanatory view for describing an example of setting of a feedback target range based on a relative speed of an object. A feedback target range 271 is set regarding an object 272 that approaches the user. A feedback target range 273 is set regarding an object 274 that recedes from the user. As illustrated in FIG. 10, the feedback target range 271, which is set regarding the object 272 that approaches the user fast, is set to have a large maximum distance. Therefore, the information processing apparatus 1 can have enough time to output a warning and can secure sufficient time for the user to avoid collision. Therefore, the user can avoid an object such as a running vehicle which the user cannot easily avoid even in a case where the user detects existence thereof by using a white cane. Meanwhile, the feedback target range 273, which is set regarding the object 274 that approaches the user slowly (in this example, recedes from the user), is set to have a small maximum distance. Therefore, it is possible to omit a warning regarding an object that takes a long time to cause danger of collision or is not dangerous because the object recedes from the user. Therefore, for example, a warning is omitted in a case where the user walks at the same pace as that of a person walking ahead of the user, and therefore the user can walk with no stress.

Note that, as illustrated in FIG. 10, the information processing apparatus 1 may set a different feedback target range for each object.

(4) Other Examples

Input Information Regarding User

For example, the information processing apparatus 1 may set a feedback target range on the basis of behavior information of the user. For example, the information processing apparatus 1 may set a small maximum distance in a case where the user is walking and may set a large maximum distance in a case where the user is running. Further, the information processing apparatus 1 may set a feedback target range in the horizontal direction in a case where the user is walking, may set a feedback target range on the ground side from the horizontal direction in a case where the user is descending stairs, and may set a feedback target range on a ceiling side from the horizontal direction in a case where the user is ascending stairs.

For example, the information processing apparatus 1 may set a feedback target range on the basis of biological information or emotional information of the user. For example, the information processing apparatus 1 may set a small maximum distance in a case where the user is tense because it is difficult for the user to pay attention to what exists ahead of the user and may set a large maximum distance in a case where the user is relaxed.

For example, the information processing apparatus 1 may set a feedback target range on the basis of feedback from the user. For example, in a case where the user tends to ignore warnings, the information processing apparatus 1 may set a small maximum distance so that the user is only warned of a truly dangerous obstruction.

For example, the information processing apparatus 1 may set a feedback target range on the basis of profile information of the user. For example, in a case where the user is an elderly person, the information processing apparatus 1 may set a large maximum distance in order that there may be enough time to compensate for a slow reaction speed.

For example, the information processing apparatus 1 may set a feedback target range on the basis of a fixation point of the user in a case of an able-bodied person and a position of a tip of a white cane in a case of a visually impaired person. For example, the user can recognize an obstruction existing at the fixation point or the position of the tip of the white cane, and therefore the information processing apparatus 1 may turn off feedback (i.e., exclude an object existing at the fixation point or the position of the tip of the white cane from targets that the user is warned of).

Input Information Regarding Object

For example, the information processing apparatus 1 may set a feedback target range on the basis of hardness of an object. For example, an influence of collision with a hard object is large, and therefore the information processing apparatus 1 may set a large maximum distance in order that there may be enough time for avoiding motion.

Input Information Regarding Environment

For example, the information processing apparatus 1 may set a feedback target range on the basis of a place where the user exists. For example, in a case where the user is on a train, the information processing apparatus 1 may set a small maximum distance in order to prevent excessive warnings in the crowded train.

For example, the information processing apparatus 1 may set a feedback target range on the basis of illuminance. For example, in a case where the user is a mildly visually impaired person or able-bodied person, the user can exhibit satisfactorily good eyesight in a bright place, and therefore the information processing apparatus 1 may set the maximum distance to 0 (i.e., turn off the feedback function).

For example, the information processing apparatus 1 may set a feedback target range on the basis of a relationship between a current place and a behavior history. For example, regarding a place where the user has recently visited or a familiar place, the user has already grasped a surrounding obstruction, and therefore the information processing apparatus 1 may set a small maximum distance. Note that the familiar place is, for example, the inside of the user's office, house, or the like.

For example, the information processing apparatus 1 may set a feedback target range on the basis of a peripheral situation. For example, the information processing apparatus 1 may set a large maximum distance in an environment in which a density of objects (e.g., people, or vehicles, or the like) existing in a surrounding environment is low. Further, in a case where a person who guides or assists the user exists in the vicinity of the user, the information processing apparatus 1 may set a small feedback target range (e.g., small maximum distance).

For example, the information processing apparatus 1 may set a feedback target range on the basis of time. For example, the information processing apparatus 1 may set a larger maximum distance at night than in the daytime in order to prevent crimes.

Input Information Regarding Device

For example, the information processing apparatus 1 may set a feedback target range on the basis of a residual quantity of a battery. For example, the information processing apparatus 1 may set a large maximum distance in a case where the residual quantity of the battery is large and may set a small maximum distance in a case where the residual quantity of the battery is small.

Control Example Based on Other Input Information

For example, the information processing apparatus 1 may control feedback on the basis of a degree of urgency. For example, the information processing apparatus 1 may change a strength of vibration by the vibrator 30, an interval of vibration, and a vibrator 30 to be vibrated among a plurality of vibrators 30 on the basis of seriousness of the degree of urgency. Note that the degree of urgency may be estimated on the basis of a relative distance, a relative speed, hardness of an object, or the like. For example, the degree of urgency may be estimated to be higher as the relative distance is shorter, a speed at which the object approaches the user is faster, and the object is harder.

For example, the information processing apparatus 1 may switch a processing content on the basis of the temperature of the CPU. For example, in a case where the temperature of the CPU is high, the information processing apparatus 1 may perform low-load processing, for example, may set a small maximum distance.

Note that the information processing apparatus 1 may switch a distance measurement method on the basis of weather. For example, the information processing apparatus 1 may switch from the distance measurement sensor using an ultrasonic wave to a depth sensor in the rain because a speed of sound may be changed because of weather. The same applies to a condition that may change a speed of sound, such as an air temperature.

For example, the information processing apparatus 1 may control feedback on the basis of a mounting place of the information processing apparatus 1 (in particular, the output unit 120). For example, on the basis of easiness of perception, the information processing apparatus 1 may vibrate for a short time in a case of being mounted on a head and may vibrate for a long time in a case of being mounted on an arm.

<<4. Conclusion>>

Hereinabove, an embodiment of the present disclosure has been described in detail with reference to FIGS. 1 to 10. As described above, the information processing apparatus 1 according to the present embodiment sets a feedback target range in which an object existing thereinside serves as a target to be fed back to the user on the basis of acquired input information, and outputs information regarding the set feedback target range to the output unit. With this, the user can receive a warning regarding an obstruction with which the user probably collides and does not receive an unnecessary warning regarding an obstruction with which the user improbably collides. Further, an appropriate feedback target range is automatically set, and therefore the user can omit manual setting of a feedback target range based on a situation of the user himself/herself, and therefore convenience is improved.

The preferred embodiment(s) of the present disclosure has/have been described above with reference to the accompanying drawings, whilst the present disclosure is not limited to the above examples. A person skilled in the art may find various alterations and modifications within the scope of the appended claims, and it should be understood that they will naturally come under the technical scope of the present disclosure.

For example, each of the devices described in the present specification may be realized as a single device, or a part of or all the devices may be realized as separate devices. For example, in the functional configuration example of the information processing apparatus 1 illustrated in FIG. 3, the storage unit 130 and the processing unit 140 may be provided in a device such as a server connected to the input unit 110 and the output unit 120 via a network or the like. Further, for example, in the functional configuration example of the information processing apparatus 1 illustrated in FIG. 3, the storage unit 130 and the processing unit 140 may be provided in a smartphone, the input unit 110 may be provided in eyeglasses, and the output unit 120 may be provided in the eyeglasses and a smartwatch.

Further, an object may be an actual object or may be a virtual object.

Further, in the above embodiment, regarding setting of a feedback target range, a maximum distance has been mainly described. However, a maximum angle and a minimum distance may also be changeably set.

Further, the methods of setting a feedback target range based on various kinds of input information, which have been described in the above embodiment, may be appropriately combined.

Note that it is not necessary for the processes described in this specification with reference to the flowchart and the sequence diagram to be executed in the order shown in the flowchart or the sequence diagram. Some processing steps may be performed in parallel. Further, some of additional steps can be adopted, or some processing steps can be omitted.

Further, the effects described in this specification are merely illustrative or exemplified effects, and are not limitative. That is, with or in the place of the above effects, the technology according to the present disclosure may achieve other effects that are clear to those skilled in the art from the description of this specification.

Additionally, the present technology may also be configured as below.

(1)

An information processing apparatus including a processing unit configured to set, on a basis of acquired input information, a feedback target range in which an object existing on inside serves as a target to be fed back to a user, in which the processing unit outputs information regarding the set feedback target range to an output unit.

(2)

The information processing apparatus according to (1), in which the processing unit outputs information regarding the object existing in the feedback target range.

(3)

The information processing apparatus according to (1) or (2), in which the processing unit outputs information indicating the set feedback target range.

(4)

The information processing apparatus according to any one of (1) to (3), in which the input information includes information regarding sensor information.

(5)

The information processing apparatus according to any one of (1) to (4), in which the input information includes information regarding a distance between the user and the object.

(6)

The information processing apparatus according to (5), in which the processing unit sets a first threshold and sets, as the feedback target range, a range in which the distance from the user is less than or equal to the first threshold or is less than the first threshold.

(7)

The information processing apparatus according to (6), in which the input information includes at least one of information regarding the user, information regarding the object, information regarding a device, and information regarding an environment.

(8)

The information processing apparatus according to (7), in which the information regarding the user includes information regarding a moving speed of the user.

(9)

The information processing apparatus according to (8), in which the processing unit sets the first threshold to be larger as the moving speed of the user is faster and sets the first threshold to be smaller as the moving speed of the user is slower.

(10)

The information processing apparatus according to any one of (7) to (9), in which the information regarding the user includes information regarding a posture of the user.

(11)

The information processing apparatus according to (10), in which the processing unit sets the first threshold to be smaller as the user is directed toward a ground side from a horizontal direction.

(12)

The information processing apparatus according to any one of (7) to (11), in which the information regarding the user includes information regarding a relative speed between the object and the user.

(13)

The information processing apparatus according to (12), in which the processing unit sets the first threshold to be larger as a speed at which the object approaches the user is faster and sets the first threshold to be smaller as the speed at which the object approaches the user is slower.

(14)

The information processing apparatus according to any one of (7) to (13), in which the information regarding the device includes information regarding a residual quantity of a battery.

(15)

The information processing apparatus according to any one of (7) to (14), in which the information regarding the environment includes information regarding a density of the objects in the vicinity of the user.

(16)

The information processing apparatus according to any one of (1) to (15), in which the processing unit sets a second threshold and sets, as the feedback target range, a range in which a distance from the user is more than or equal to the second threshold or is more than the second threshold.

(17)

The information processing apparatus according to any one of (1) to (16), in which the processing unit gradually changes the feedback target range.

(18)

The information processing apparatus according to any one of (1) to (17), in which the processing unit changeably sets a time interval between a change in the input information and a change in the feedback target range.

(19)

The information processing apparatus according to any one of (1) to (18), in which the processing unit outputs information regarding a distance measurement range indicating a range in which distance measurement is performed to a measurement unit configured to measure a distance between the user and the.

(20)

An information processing method including:

setting, by a processor to set, on a basis of acquired input information, a feedback target range in which an object existing on inside serves as a target to be fed back to a user; and outputting information regarding the set feedback target range to an output unit.

(21)

A program causing a computer to function as an information processing apparatus including a processing unit configured to set, on a basis of acquired input information, a feedback target range in which an object existing on inside serves as a target to be fed back to a user, in which the processing unit outputs information regarding the set feedback target range to an output unit.

(22)

An information processing apparatus including a control unit configured to set, on a basis of acquired input information, a distance measurement range indicating a range in which a distance from a position of a user to an arbitrary object is measured, in which the control unit outputs information regarding the set distance measurement range to a distance measurement unit.

(23)

The information processing apparatus according to (22), in which the input information includes information related to sensor information.

(24)

The information processing apparatus according to (22) or (23), in which the input information is information regarding a moving speed of a user.

(25)

The information processing apparatus according to (4), in which the distance measurement range is set on a basis of a maximum measurement distance from the position of the user, and, in a case where the moving speed of the user is higher than a predetermined speed, the maximum measurement distance is set to a first value, and, in a case where the moving speed of the user is lower than the predetermined speed, the maximum measurement distance is set to a second value different from the first value.

(26)

The information processing apparatus according to (25), in which the first value is larger than the second value.

(27)

The information processing apparatus according to (22) or (23), in which the input information is information regarding a posture of the user.

(28)

The information processing apparatus according to (27), in which the distance measurement range is set on a basis of a maximum measurement distance from the position of the user, and, in a case where the user is directed downward, the maximum measurement distance is set to a third value.

(29)

The information processing apparatus according to (22), further including a notification unit configured to notify the user of the information regarding the set distance measurement range.

(30)

The information processing apparatus according to (22), further including a distance measurement unit configured to measure a distance within the set distance measurement range.

REFERENCE SIGNS LIST

1 information processing apparatus
10 distance measurement sensor
20 electronic circuit
30 vibrator
40 battery
50 acceleration sensor
60 geomagnetic sensor
90 eyeglasses
110 input unit
120 output unit
130 storage unit
140 processing unit
141 acquisition unit
143 setting unit
145 output control unit

The invention claimed is:

1. An information processing apparatus, comprising:
a central processing unit (CPU) configured to:
acquire input information from at least one sensor,
wherein the input information includes posture information indicating a direction of head of a user of the information processing apparatus;
set, based on the posture information, a first threshold value corresponding to a first distance between the user and a first position at which an object is detectable;
set a second threshold value corresponding to a second distance between the user and a second position at which the object is detectable;
set a feedback target range based on the first distance that is one of less than or equal to the first threshold value, and the second distance that is one of more than or equal to the second threshold value, wherein the second threshold value is smaller the first threshold value, and
the object inside the set feedback target range serves as a target fed back to the user; and
output information regarding the set feedback target range to an output device.

2. The information processing apparatus according to claim 1, wherein the CPU is further configured to output information of the object in the set feedback target range.

3. The information processing apparatus according to claim 1, wherein the input information further includes information regarding a third distance between the user and the object.

4. The information processing apparatus according to claim 1, wherein the input information further includes at least one of information regarding the user, information regarding the object, information regarding a device, or information regarding an environment.

5. The information processing apparatus according to claim 4, wherein the information regarding the user includes information regarding a moving speed of the user.

6. The information processing apparatus according to claim 5, wherein the CPU is further configured to:
set the first threshold value to a first value when the moving speed of the user is a first speed; and
set the first threshold value to a second value when the moving speed of the user is a second speed slower than the first speed, wherein the second value is less than the first value.

7. The information processing apparatus according to claim 1, wherein the CPU is further configured to set the first threshold value to a minimum value when the user is directed toward a ground side from a horizontal direction.

8. The information processing apparatus according to claim 4, wherein the information regarding the user includes information regarding a relative speed between the object and the user.

9. The information processing apparatus according to claim 1, wherein the CPU is further configured to:
set the first threshold value to a first value when a speed at which the object approaches the user is a first speed; and
set the first threshold value to a second value when the speed at which the object approaches the user is a second speed slower than the first speed, wherein the second value is less than the first value.

10. The information processing apparatus according to claim 4, wherein the information regarding the environment includes information regarding a density of objects in vicinity of the user.

11. The information processing apparatus according to claim 1, wherein
the CPU is further configured to output information of a distance measurement range, and
the distance measurement range is a range in which a third distance between the user and the object is measurable.

12. The information processing apparatus according to claim 1, wherein the CPU is further configured to set the first threshold value based on at least one of a direction of travel of the user, a direction of a face of the user, or a direction of a road.

13. An information processing method, comprising:
acquiring, by a processor of an information processing apparatus, input information from at least one sensor,
wherein the input information includes posture information indicating a direction of head of a user of the information processing apparatus;
setting, by the processor, a first threshold value based on the posture information,
wherein the first threshold value corresponds to a first distance between the user and a first position at which an object is detectable;
setting, by the processor, a second threshold value corresponding to a second distance between the user and a second position at which the object is detectable;
setting, by the processor, a feedback target range based on the first distance that is one of less than or equal to the first threshold value, and the second distance that is one of more than or equal to the second threshold value, wherein
the second threshold value is smaller the first threshold value, and
the object inside the set feedback target range serves as a target fed back to the user; and
outputting, by the processor, information regarding the set feedback target range to an output device.

14. A non-transitory computer-readable medium having stored thereon computer-executable instructions that, when executed by a processor of an information processing apparatus, cause the processor to execute operations, the operations comprising:
acquiring input information from at least one sensor,
wherein the input information includes posture information indicating a direction of head of a user of the information processing apparatus;
setting, based on the posture information, a first threshold value corresponding to a first distance between the user and a first position at which an object is detectable;
setting a second threshold value corresponding to a second distance between the user and a second position at which the object is detectable;
setting a feedback target range based on the first distance that is one of less than or equal to the first threshold value, and the second distance that is one of more than or equal to the second threshold value, wherein
the second threshold value is smaller the first threshold value, and
the object inside the set feedback target range serves as a target fed back to the user; and
outputting information regarding the set feedback target range to an output device.

* * * * *